(12) United States Patent  
Miller

(10) Patent No.: US 8,900,324 B2  
(45) Date of Patent: Dec. 2, 2014

(54) SYSTEM AND METHOD FOR TREATING TISSUE WALL PROLAPSE

(75) Inventor: Dennis Miller, Shorewood, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1561 days.

(21) Appl. No.: 12/293,025

(22) PCT Filed: Mar. 15, 2007

(86) PCT No.: PCT/US2007/064093  
§ 371 (c)(1),  
(2), (4) Date: Mar. 23, 2009

(87) PCT Pub. No.: WO2007/106897  
PCT Pub. Date: Sep. 20, 2007

(65) Prior Publication Data  
US 2009/0326573 A1    Dec. 31, 2009

Related U.S. Application Data

(60) Provisional application No. 60/782,911, filed on Mar. 16, 2006.

(51) Int. Cl.
| | | |
|---|---|---|
| A61F 2/02 | (2006.01) | |
| A61F 2/00 | (2006.01) | |
| A61B 17/062 | (2006.01) | |
| A61B 17/42 | (2006.01) | |
| A61B 17/04 | (2006.01) | |
| A61B 17/00 | (2006.01) | |
| A61B 17/06 | (2006.01) | |

(52) U.S. Cl.  
CPC ..... *A61F 2/0045* (2013.01); *A61B 2017/00805* (2013.01); *A61B 2017/06028* (2013.01); *A61B 17/0625* (2013.01); *A61B 17/42* (2013.01); *A61B 17/0482* (2013.01); *A61B 2017/4225* (2013.01); *A61B 2017/00557* (2013.01)  
USPC ........................................................ 623/23.72

(58) Field of Classification Search  
USPC ........... 623/23.72; 606/151, 213, 200; 600/37  
See application file for complete search history.

(56) References Cited

U.S. PATENT DOCUMENTS

| | | | |
|---|---|---|---|
| 1,750,188 A | | 7/1928 | Mumberg |
| 1,790,801 A | | 2/1931 | Dickstein |
| 4,669,478 A | | 6/1987 | Robertson |
| 4,920,986 A | * | 5/1990 | Biswas .................. 128/885 |
| 5,364,408 A | | 11/1994 | Gordon |
| 5,458,609 A | | 10/1995 | Gordon et al. |
| 5,540,704 A | | 7/1996 | Gordon et al. |
| 5,575,800 A | | 11/1996 | Gordon |

(Continued)

FOREIGN PATENT DOCUMENTS

| | | |
|---|---|---|
| EP | 1609439 A1 | 6/2005 |
| FR | 2852817 A1 | 3/2003 |

(Continued)

*Primary Examiner* — Melanie Tyson

(57) ABSTRACT

Devices for controlling prolapse. The device includes a base, first and second lobes which protrude from a midsection of the base, and an anchoring knob distal the base. Various portions of the device are inflatable to and are inflated by way of an inflation tube and an inflation device. Some versions of the device include a base, an anchoring knob, and a shaft that extends between and connects the base and the anchoring knob, again with portions thereof being inflatable.

15 Claims, 10 Drawing Sheets

(56) References Cited

U.S. PATENT DOCUMENTS

| | | | |
|---|---|---|---|
| 5,662,664 A | 9/1997 | Gordon et al. | |
| 5,771,900 A | 6/1998 | Austin et al. | |
| 5,840,011 A * | 11/1998 | Landgrebe et al. | 600/30 |
| 6,015,417 A * | 1/2000 | Reynolds, Jr. | 606/151 |
| 6,042,534 A | 3/2000 | Gellman et al. | |
| 6,102,921 A | 8/2000 | Zhu et al. | |
| 6,273,852 B1 | 8/2001 | Lehe et al. | |
| 6,418,930 B1 | 7/2002 | Fowler | |
| 6,460,542 B1 | 10/2002 | James | |
| 6,612,977 B2 | 9/2003 | Staskin et al. | |
| 6,638,284 B1 | 10/2003 | Rousseau et al. | |
| 6,808,487 B2 | 10/2004 | Migliari | |
| 6,911,003 B2 | 6/2005 | Anderson et al. | |
| 6,936,952 B2 | 8/2005 | Takamine | |
| 7,131,943 B2 | 11/2006 | Kammerer | |
| 7,794,385 B2 * | 9/2010 | Rosenblatt | 600/30 |
| 2002/0099259 A1 | 7/2002 | Anderson et al. | |
| 2003/0220538 A1 | 11/2003 | Jacquetin | |
| 2004/0015048 A1 | 1/2004 | Neisz et al. | |
| 2004/0039453 A1 | 2/2004 | Anderson et al. | |
| 2005/0222591 A1 | 10/2005 | Gingras et al. | |
| 2005/0234291 A1 | 10/2005 | Gingras | |
| 2005/0261545 A1 | 11/2005 | Gellman et al. | |
| 2005/0278037 A1 | 12/2005 | Delorme et al. | |
| 2005/0288706 A1 * | 12/2005 | Widomski et al. | 606/213 |
| 2006/0052801 A1 | 3/2006 | Dreyfuss et al. | |
| 2006/0058575 A1 | 3/2006 | Zaddem et al. | |
| 2007/0173864 A1 | 7/2007 | Chu | |

FOREIGN PATENT DOCUMENTS

| | | |
|---|---|---|
| FR | 2871365 A1 | 6/2004 |
| MX | PA04008407 A | 8/2004 |
| WO | 0231681 | 4/2002 |
| WO | 03073960 A1 | 9/2003 |
| WO | 03096929 A1 | 11/2003 |
| WO | 2004091442 A2 | 10/2004 |
| WO | 2004091443 A2 | 10/2004 |
| WO | 2005110272 A2 | 11/2005 |
| WO | 2007014240 A1 | 2/2007 |
| WO | 2007016698 A3 | 2/2007 |

* cited by examiner

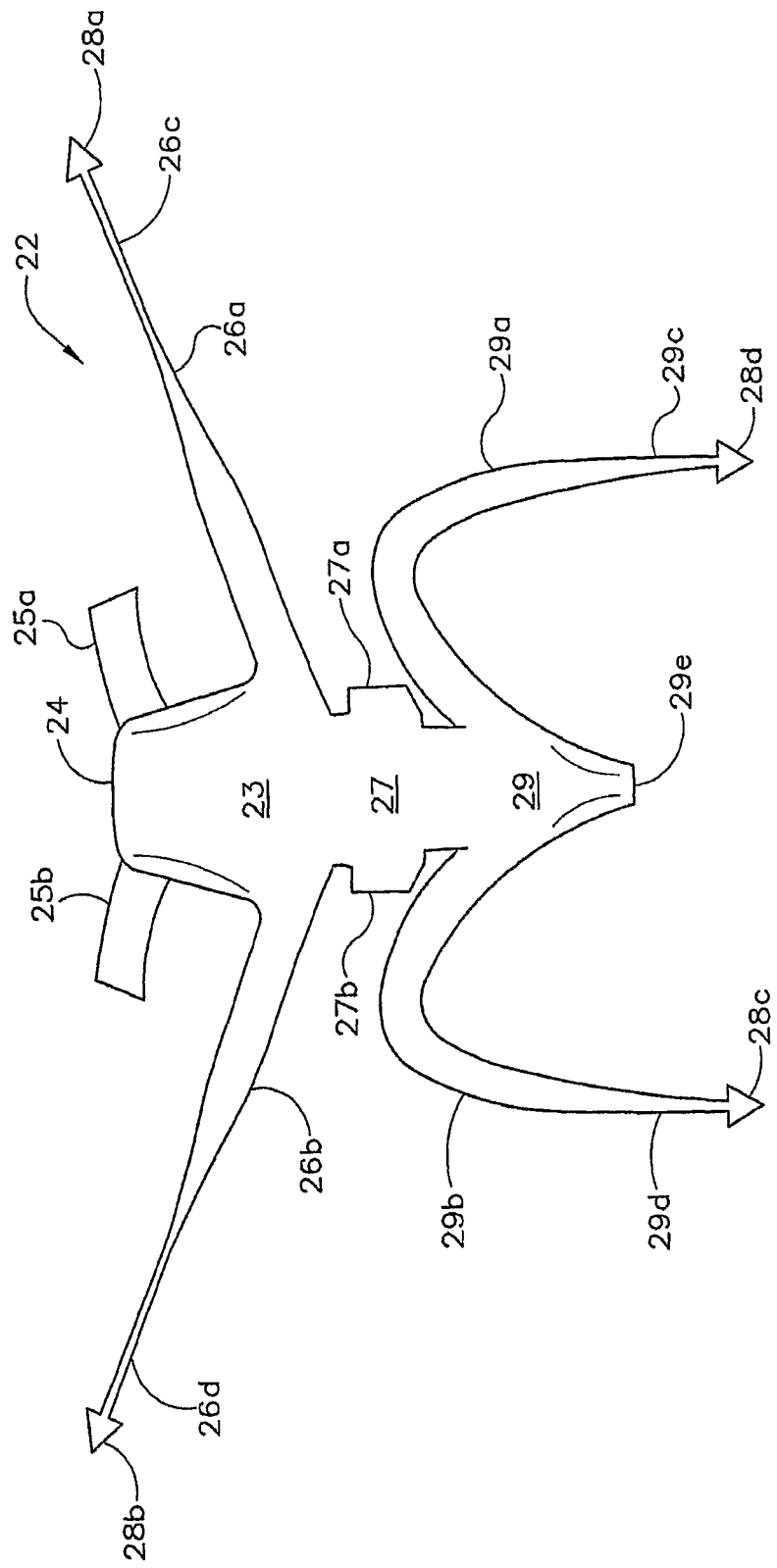

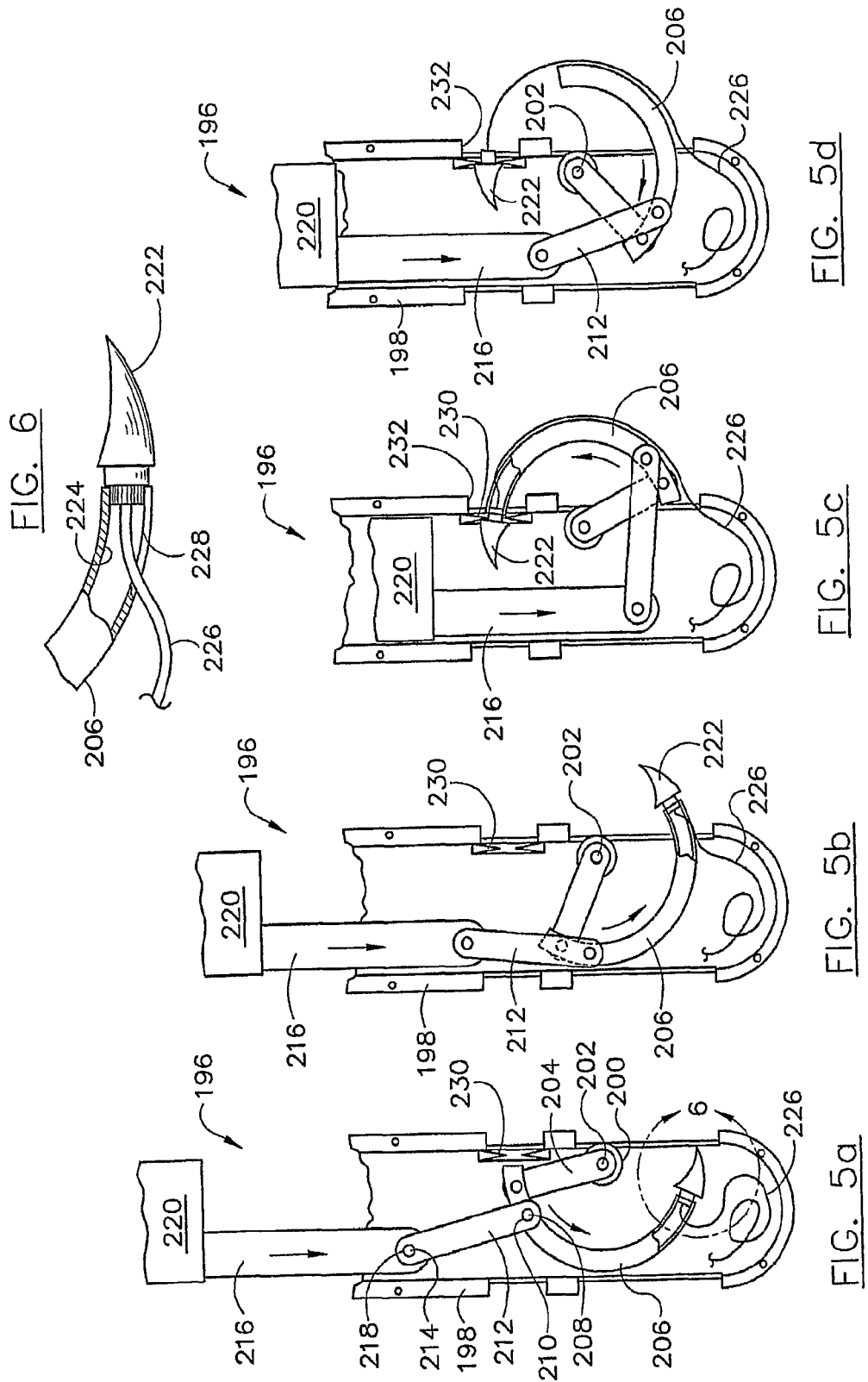

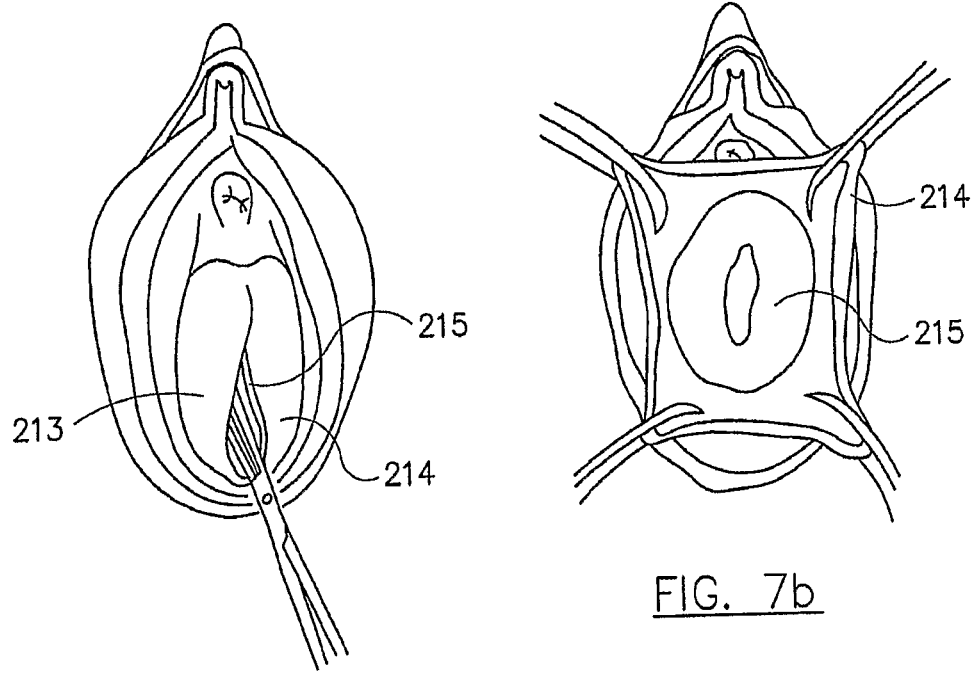
FIG. 7a
FIG. 7b
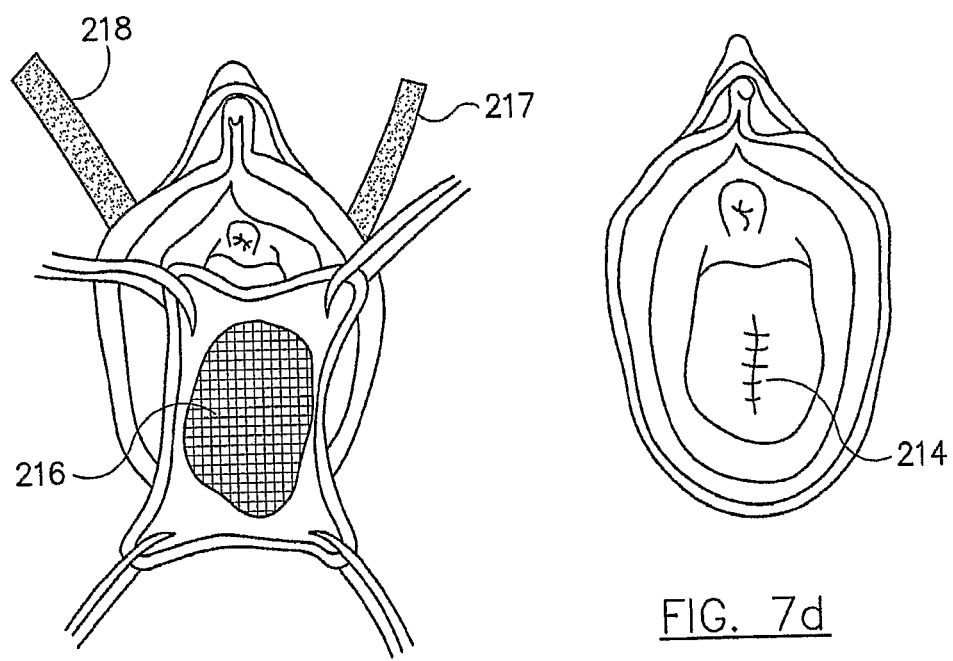
FIG. 7c
FIG. 7d

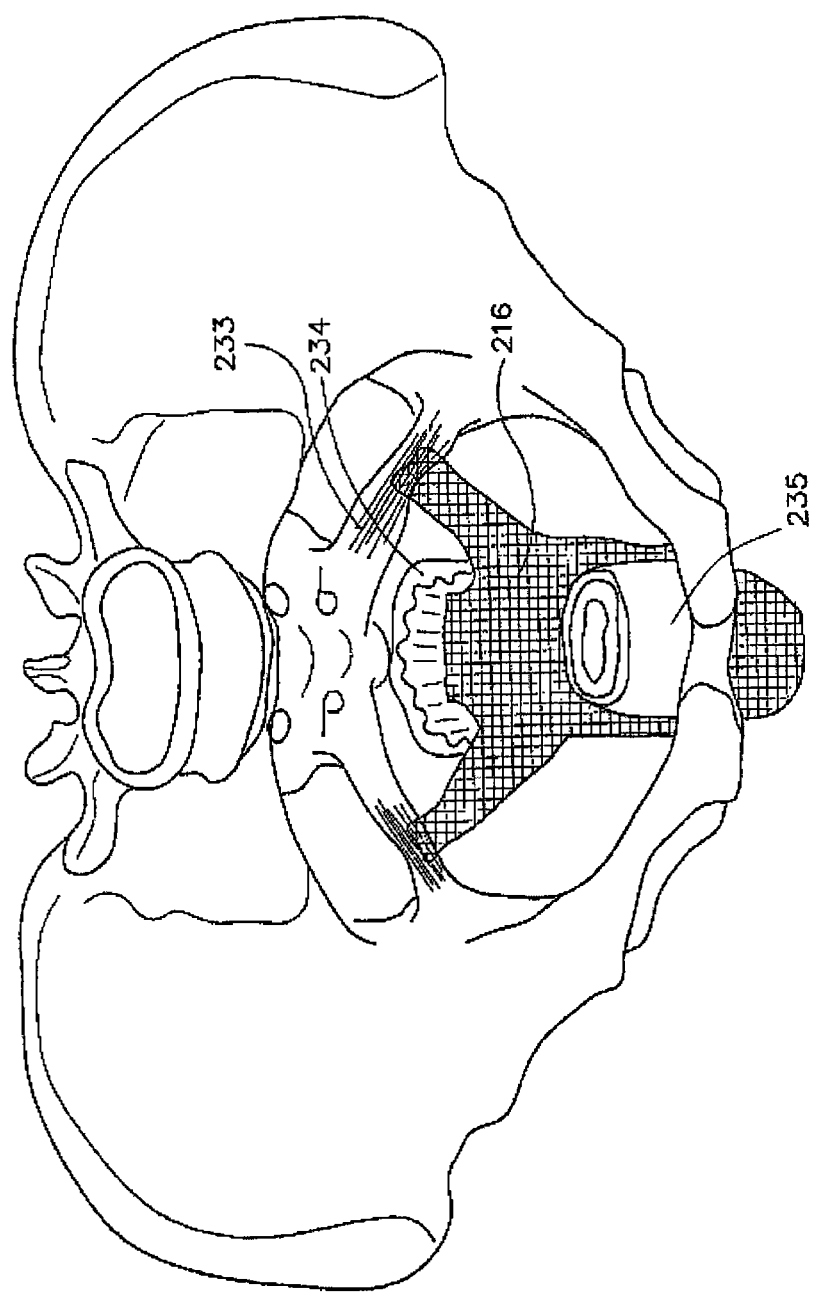

SYSTEM AND METHOD FOR TREATING TISSUE WALL PROLAPSE

CROSS-REFERENCE TO RELATED APPLICATIONS

This application claims priority to International Application No. PCT/US2007/064093, filed on Mar. 15, 2007, which is hereby expressly incorporated herein by reference.

This application claims priority from U.S. Provisional Patent Application Ser. No. 60/782,911, filed on Mar. 15, 2006, the entirety of which is expressly incorporated by reference herein in its entirety.

BACKGROUND OF THE INVENTION

1. Field of the Invention

The present invention relates in general to a system and method in the field of prolapse treatment. More particularly, the present invention relates to an apparatus with multiple components and method for correcting tissue wall prolapse using the same. Specifically, a preferred embodiment of the present invention is a kit that has at least a pessary.

2. Discussion of the Related Art

As is known to those skilled in the art, the treatment of vaginal wall prolapse has been hampered by high failure rates. The main reasons for failure have been the inherent weakness of the tissue being re-approximated and the inability of the repair to withstand the forces applied by the abdominal cavity bearing down from above. In the last decade, one major advance in repair has been the addition of grafts to reinforce those repairs. While this phenomenon has been gaining wide spread acceptance, there lacks a consensus regarding how to affix the graft under the vaginal wall to best maintain durability and vaginal caliber. Note that vaginal caliber is important because of its impact on sexual function.

Unfortunately, with current procedures, the graft is at risk for being dislodged over time. For example, when the graft is sewn into place with standard sutures over the pelvic floor muscles, it is prone to cause pain from suture entrapment. Further, there is concern that sutures may be prone to pullout. This is especially true since the tissues the sutures are placed in are thin and inherently weak. Finally, the placement of the sutures is variable from surgeon to surgeon. This causes an impact on teaching proper graft placement.

All of the above issues may affect the success of the repair. Therefore, there is now greater interest in new ways of affixing and maintaining grafts. As a result, several recent procedure iterations have become available on the market in this regard.

With the introduction of new techniques, several improved devices, such as the Prolift™ device from Ethicon, Inc., have been made commercially available. Other commercial device kits are available in this field for prolapse repair that compete with Prolift™, for example, American Medical Systems' Apogee™ and Perigee™ system, Tyco's IVS Tunneller™ system, and Bard's Avaulta™ system. In general, these systems utilize medical mesh with wings at the corners so that the mesh may be drawn through the pelvic floor musculature and pelvic ligaments to secure the mesh.

A well-accepted access point to securing the wings of these systems has been through the obturatormembrane and ischiorectal fossa. Access is generally made viathese structures because the apex of the vagina is located deep with the pelvis. However, the problem with accessing the apex via these structures is that this anatomy is unfamiliar to surgeons. Further, safety remains a concern for surgeons because these systems require the passage of sharp needles long distances through these unfamiliar anatomic. Thus, extensive training and anatomy education is required to properly learn the technique. As a result, only a small number of surgeons have actually adopted these techniques.

The patents and publications of general interest here include: U.S. Pat. Nos. 6,936,052; 5,364,408; 5,458,609; 5,575,800; 5,662,664; 5,540,704; 6,470,890; U.S. Pat. Pub. Nos. 2005/0261545 and 2006/0052801; WO 2002/078568A1; WO 2003/028585A1; WO 2002/078552A1; and WO2004/045457A1. These patents and published applications disclose embodiments that were at least in part satisfactory for the purposes for which they were intended. The disclosures of all of these patents and applications in their entireties are hereby expressly incorporated by reference into the present application for purposes including, but not limited to, indicating the background of the present invention and illustrating the state of the art.

In general, the embodiments disclosed in the above-referenced patents and publications have the disadvantage that they are in general difficult or dangerous to use without extensive training. Also, they are only partially effective to treat prolapse. Other disadvantages include increased risk and ineffective results over time. For example, after sutures are made, the vagina is traditionally packed with gauze. This leads to significant discomfort after surgery. If the gauze is not removed within 24 hours, infection and other problems may develop.

Given the above, patients suffering prolapse either must wait long periods of time for treatment or forego the same altogether because of the risk involved and the necessary high-level of surgeon skill. It should be noted also that only a fraction of the hundreds of thousands of patients getting prolapse repair surgery are availed to the latest technology. This further leads to a procedure with a relatively high cost.

Therefore, what is needed is a relatively simple system and method. Further, what is also needed is a system and method that are easily repeatable and highly effective over time.

SUMMARY AND OBJECTS OF THE INVENTION

By way of summary, the present invention is directed to preferably a system that includes a kit. The kit preferably has a post—operative pessary. Other components may include a pre-cut shaped mesh graft, and a graft delivery device. The present invention also includes a method of using the kit to repair a vaginal prolapse.

A primary object of the invention is to provide an apparatus that reduces patient discomfort. Another object of the invention is to provide a system that is ruggedized and reliable. Another object of the invention is to provide an apparatus that has one or more of the characteristics discussed above but which is relatively simple to implant without too much additional training.

Another object of the invention is to provide a method that can be used to prevent recurring prolapse. Another object of the invention is to provide a method that is predictable and reproducible, thereby increasing success rates and decreasing risk, pain, variance, recovery time, and medical costs. Another object of the invention is to provide a method that has one or more of the characteristics discussed above but which is relatively simple to set up and perform.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which:

FIGS. 2, 2a-2c shows the graft of the kit of the present invention;

FIGS. 4a, 4b, 5a, 5b, 5c, 5d and 6 show the operation of the graft placement component of FIG. 3a having a bullet needle and thread of the graft of FIG. 2 attached thereto;

FIGS. 7a-7d show an incision being made in the vaginal wall and the muscle and flesh pulled back and show the incision after the graft has been inserted and the incision has been sutured; and FIG. 8 shows various parts of the anatomy with some components of the system of the present invention in place.

Figure 1A:
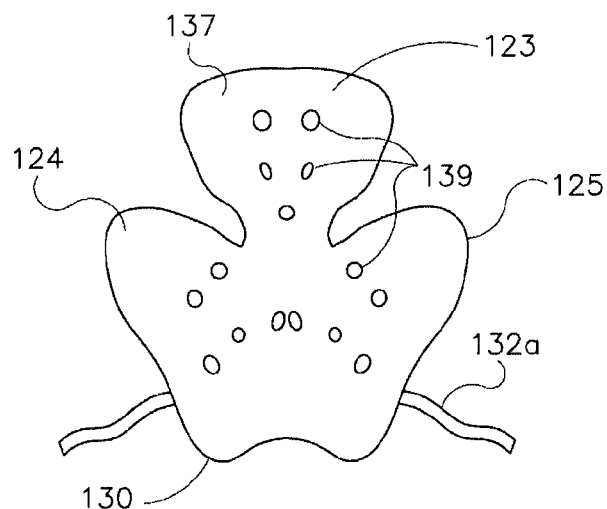
FIG. 1a illustrates the top plan view of the pessary component of the kit of the present invention.

In describing the preferred embodiment of the invention that is illustrated in the drawings, specific terminology will be resorted to for the sake of clarity. However, it is not intended that the invention be limited to the specific terms so selected and it is to be understood that each specific term includes all technical equivalents that operate in a similar manner to accomplish a similar purpose. For example, the word "connected" or terms similar thereto are often used. They are not limited to direct connection but include connection through other elements where such connection is recognized as being equivalent by those skilled in the art.

DESCRIPTION OF EMBODIMENTS

The present invention and the various features and advantageous details thereof are explained more fully with reference to the non-limiting embodiments described in detail in the following description.

1. System Overview

This invention, which includes elements of a method and device, represents a novel Way of treating vaginal wall prolapse. Prior art, as discussed above, is inadequate and limited By complexity of use, etc.

The present invention is a system that preferably includes a kit to overcome the above-mentioned limitations. The kit preferably has at least one main component: an optional inflatable post-operative pessary. The pessary shown in U.S. Pat. No. 6,470,890 (incorporated herein by reference) is similar. However, the present invention is a unique inflatable post-operative pessary device, shaped to mirror the shape of the vagina and to capitalize on surfaces of the vagina that will aid in retention. This invention may be a line extension of the traditional pessary device although here it acts as a vaginal splint during surgical healing (i.e., for keeping the mesh back as far as it will go). This splint could also be used non-surgically as a replacement for standard pessaries. Note Mentor and Milex make the majority of currently used pessaries. However, such prior art designs are fundamentally decades old and suffer from difficulty with insertion and retention. Moreover, the firm shapes of such previous pessaries create an increased probability of pressure sores on the vagina and are not used as post-operative vaginal splints for this reason.

In one preferred embodiment, the kit may also include a synthetic polypropylene mesh graft version that is similar to the mesh of the Prolift™ system produced in a kit form by Ethicon, Inc. One patent associated with this system is for the specific graft used, that being a synthetic polypropylene mesh shown and described in U.S. Pat. No. 6,638,284 which is herein incorporated by reference. Similar to the Prolift™ graft, the inventive graft is preferably designed to cover the entire vaginal vault and provide anchoring to the Arcus Tendineous and Sacrospinous Ligament.

Another component may be a graft placement component or delivery device. The inventive delivery device is preferred blade trocar similar to the ones illustrated in U.S. patent numbers mentioned above. For example, such a "Laurus™" or "Capio™" device may be a good predicate device for the delivery device component of this kit. The graft delivery device acts preferably as a suture-capturing device also but here the suture is a mesh wing.

Using the components described above, the inventive method includes the following steps: make an incision in the vaginal wall; open the incision to gain access inside the vagina and Pelvic Floor; take a suture-capturing device in hand; attach the mesh wing; insert the wing; push the wing through the ligaments; pull the wing back out the cut hole with the suture device; attach another wing; and repeat the process at another location within the vagina; repeat the process with the other wings until all of the wings are attached to commonly accepted apical and lateral support structures. These are generally the Sacrospinous Ligament and proximal Arcus tendineus. This tension-free wing securement allows the custom adjustment for each patient, which would not occur with suture fixation. The excess mesh wing material should then be trimmed away and discarded. After the remaining mesh is secured, the incision is closed, an inventive pessary device is then inserted into the vagina and inflated. The pessary holds the mesh in place and also allows healing to take place so that the mesh becomes embedded into the vaginal wall. The pessary preferably stays in place over a period of time, for example, three to ten days.

2. Detailed Description of the Preferred Embodiments

As mentioned above, the system of the present invention in one embodiment is a kit preferably having main parts.

Figure 1B:
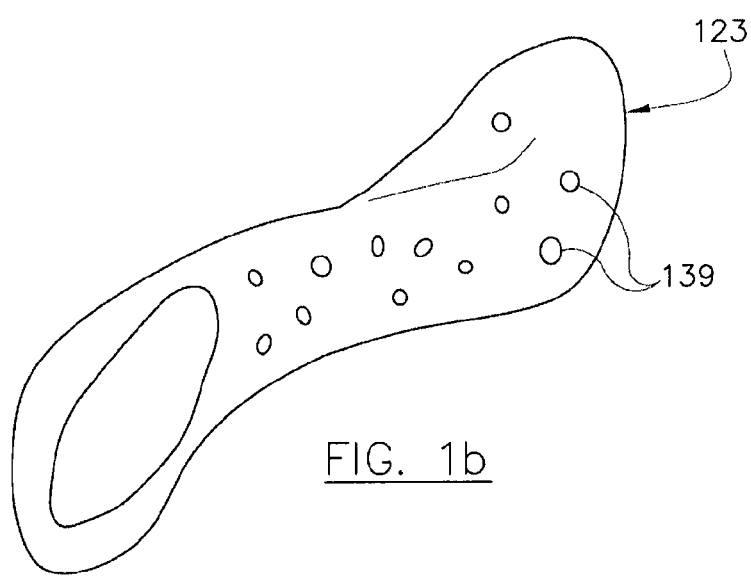
FIG. 1b illustrates the side view of the pessary component of the present invention.
Figure 1C:
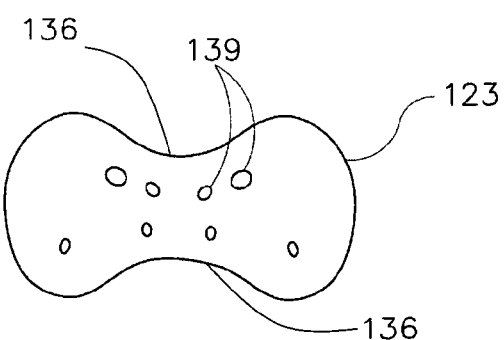
FIG. 1c illustrates the end view of the pessary component of the present invention.

The first component is a pessary. As shown in FIGS. 1a-1c, as pessary 123 of the present invention, which preferably has a configuration designed to hold it in place within the vaginal cavity. Further, while a limited number of inflatable pessaries are currently available, they are shaped in ways that reduce retention since they do not capitalize on the aspects of the vagina and pelvic floor muscles that could be used to increase retention in the vaginal vault. See, for example, WO 2004/045457 herein incorporated by reference. However, the inventive pessary component is constructed and shaped to overcome the limitations found in the prior art. See, e.g., Figs 1a-1c.

The inventive pessary further may have a bumpy or dimpled surface to aid in retention to the wall tissue. The pessary is preferably made of pliable material such as a soft polymer, e.g., rubber, a non-latex, or silicone. In one preferred embodiment, the pessary is preferably an inflatable pessary. The pessary is used as a splint after surgery to temporarily hold the mesh in place until it physically bonds to the interior vaginal wall. In one alternative embodiment the pessary may have a shape like that of a Gellhorn™ pessary, but instead of being made of a solid silicone it may be inflatable.

At the present time, pessaries are rarely used as a post-operative splint to help maintain the position of a vaginal surgical repair. Currently, surgeons most often use gauze packing for that purpose, which is significantly limited by the need to remove it after a short period of time and the relative discomfort associated with its use. The other significant limitation is that the packing compresses the urethra, reducing the patient's ability to void until it is removed.

Only Mentor has a pessary for surgical use called an "adjustable vaginal stent". However, this post-operative splint has fallen into disuse because its oblong tubular shape is inefficient for the dissimilarly shaped vagina and retention rates are poor as a result. Interest in splinting the vagina has been renewed because a graft reinforced vaginal repair creates a greater need to support the vagina during healing. These grafted procedures often utilize less tacking sutures and rely on the resistance to displacement of the material to maintain its position while healing.

There has been some attempt to design pessaries to serve as a post-operative splint. However, design deficiencies cause the devices to be poorly retained if not sewn in or cause pressure spots and pain if the traditional shapes are used. This is primarily because they were designed without correct understanding of the actual shape of the vagina in a live ambulatory woman and a lack of understanding of the best retention points within the vaginal cavity. Recent use of MRI 3D reconstructed images has furthered understanding of these issues.

Further, prior art inflatable pessaries lack the properties of good retention because they fail to achieve a shape, which mirrors the shape of the vaginal cavity. They also fail to capitalize on the retention points created by the shape of the Levator Ani muscle as it surrounds the midvagina.

The inventive pessary device 123 is novel in that the design is created to improve retention without increasing the pressure within the vagina. Being inflatable and appropriately shaped also allows it to evenly distribute the pressure of the vaginal walls. Rather than having the circular or symmetrically tubular shape of prior art, the pessary 123 possesses an arc to minor the posterior axis deviation of the vagina and has a horizontally ovoid cross-sectional shape. In one embodiment, the shape resembles a mushroom or toggle bolt with a banana shaped axis. Such a shape allows the pessary to be better "captured" behind the Levator Ani within the midvagina.

The pessary 123 further has a first lobe 124, second lobe 125, a base 130, an inflation tube 132a, and an anchoring knob 137. Preferably, a slight central depression 136 is present to keep pressure off the surgical sites when used post-operatively. In use, the inflated lobes or flanges 124, 125 protrude from the midsection to lodge behind the Levator margin. The knob 137 is convex to elevate the anterior wall. The inflation access or tube 132a will protrude from a distal end and inflate with a standard inflation device. A variety of connectors could be added to it. Dimples or bumps 139 may also be present.

Figure 9A:
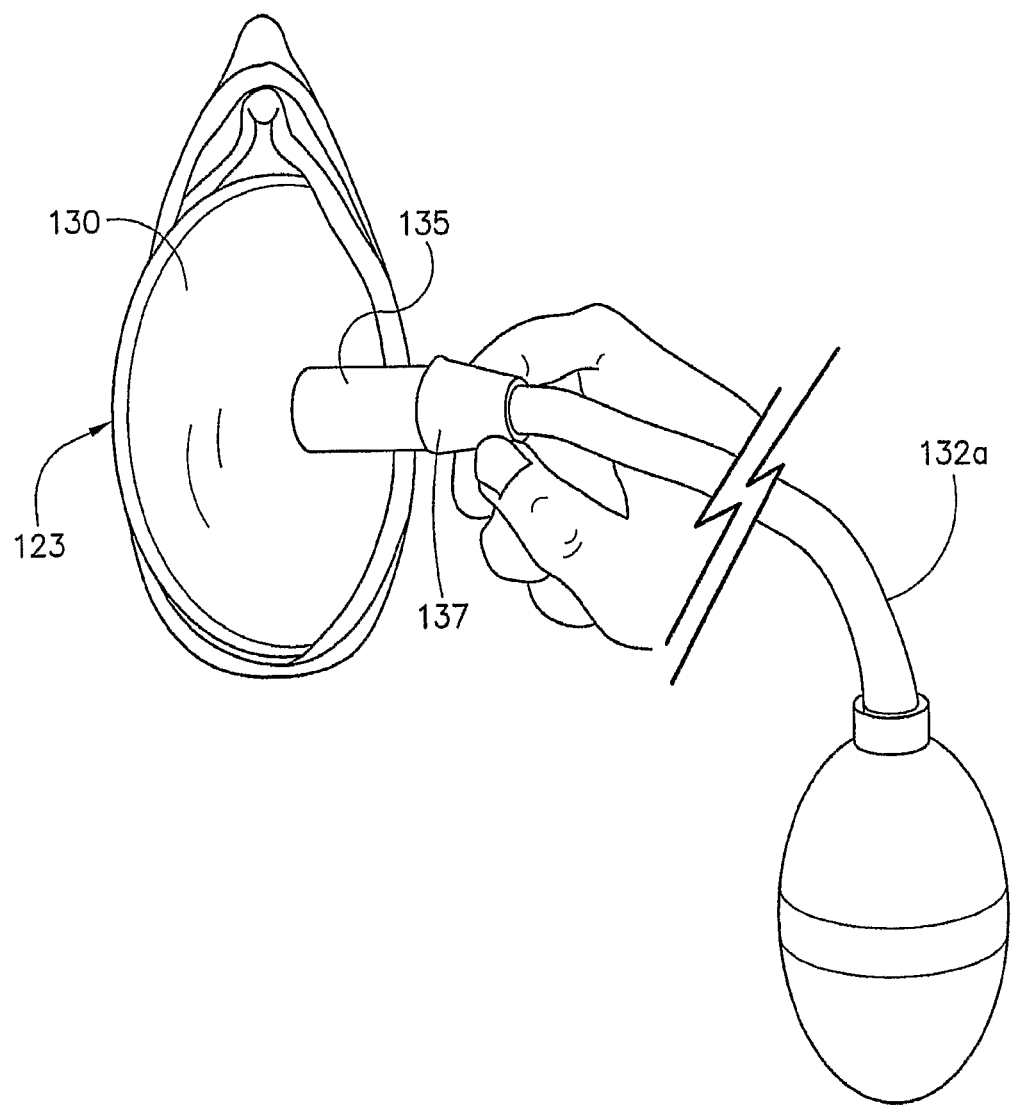
FIG. 9a shows a pictorial view of an alternative embodiment of the pessary of the present invention, being vaginally inserted.
Figure 9B:
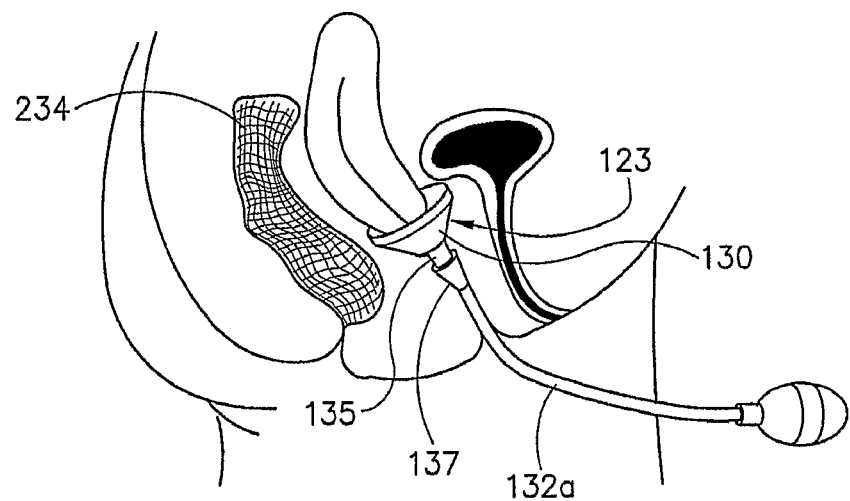
FIG. 9b shows various parts of the anatomy with some components of the system of FIG. 9a in place.
Figure 9C:
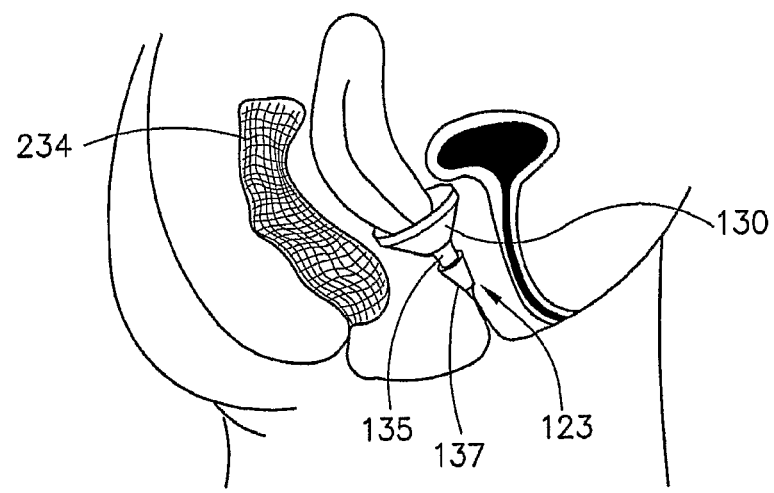
FIG. 9c shows various parts of the anatomy with some components of the system of FIG. 9a in place, with the inflation tube removed.

FIGS. 9a-9c show various other configurations of the pessary 123. In FIGS. 9a-9c, e.g., the pessary 123 includes a base 130, an inflation tube 132a, an anchoring knob 137, and a shaft 135 that extends between and connects base 130 and anchoring knob 137. In use, any of base 130, shaft 135, and anchoring knob 137; or, optionally, more than one or all of base 130, shaft 135, and anchoring knob 137 can be inflated by way of a standard inflation device, such as the illustrated bulb inflator.

There are several extensions to this use of this device 123. It is estimated that only a small fraction of patients with prolapse are operated upon. For a large number of patients, surgery is undesirable or not possible. The only alternative for those women is the traditional rigid pessary devices that are used in a small number of patients. Similar to the concerns with post-operative use, these devices are difficult to fit and are associated with uneven pressure distribution. There is an inflatable pessary (e.g., Inflatoball™- Milex, Inc.) that solves these dilemmas but its spherical shape makes retention more difficult. This inventive pessary 123 could be used in its place and would solve these problems with a design that aids retention without making insertion more difficult or cause skin irritation. One important aspect to this inventive design is that it allows a ventral protuberance to be fashioned under the urethra. This could be used for its ability to non-surgically treat urinary incontinence. Current pessaries that purport to treat stress incontinence with a ventral protuberance often fail because the circular shape fails to keep the position of the protuberance constant and it shifts away from the desired suburethral location.

The future uses of this pessary could be to evenly deliver therapies through its uniform contact with the vagina. Drugs or even electrical stimulation can be delivered transdermally through this device.

The next kit component is a preferably a graft. As best shown in FIGS. 2-2c, the mesh has a unique shape. Turning to FIG. 2, in this embodiment, the inventive graft here is a mesh 22 having protrusions referred to as arms, legs, and wings (or generally "wings"). The inventive mesh 22 preferably includes an upper portion 23, first edge 24, first optional wing 25a, second optional wing 25b, third wing 26a, and fourth wing 26b. Preferably, a first needle connecting segment 26c, a second needle connecting segment 26d, a central body portion 27, a first arm 27a, and a second arm 27b also make up the mesh 22. The mesh 22 may further include a lower portion 29, a first leg 29a, a second leg 29b, a third connecting segment 29c, a fourth connecting segment 29d, and a tail 29e. On each arm and leg respectively is preferably a first bullet needle 28a, second bullet needle 28b, third bullet needle 28c, and fourth bullet needle 28d. In another embodiment, wings 25a and 25b are not present.

The inventive wings, legs, arms, etc. are intended to be used for attachment via the Arcus Tendineous near the Ischial Spine for the anterior vaginal wall and the Sacrospinous Ligament on the posterior vaginal wall. These anatomical structures are deep in the pelvis making them excellent for support but otherwise difficult to access without a special graft delivery device as will be described more fully below. However, once such a device reaches the preferred location, the device helps the surgeon to wedge the graft mesh into place.

Figure 2A:
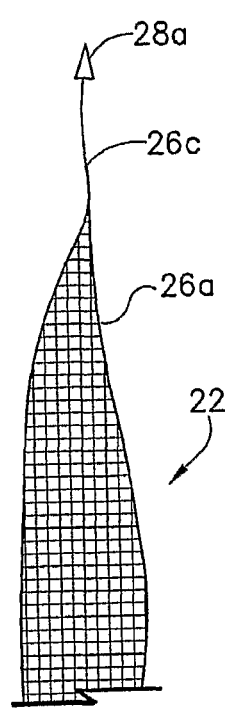
Figure 2B:
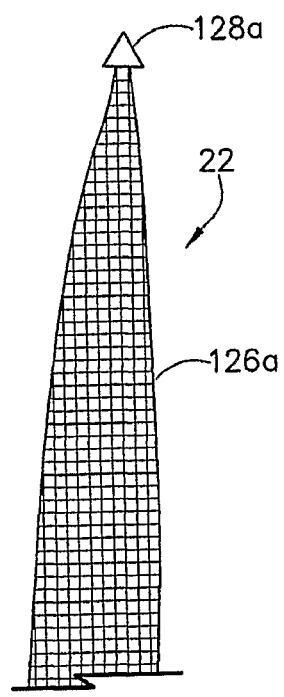
Figure 2C:
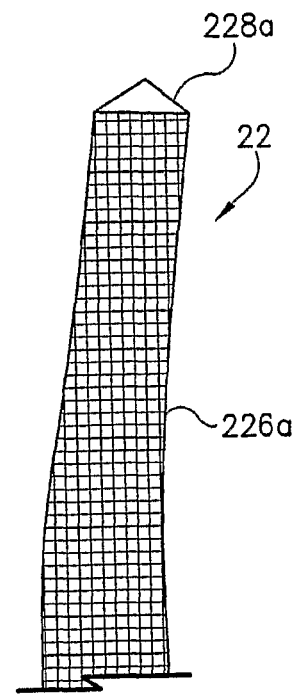

FIGS. 2a-2c show various preferred configurations of the bullet needle and the leg or arm. In FIG. 2a, e.g., the bullet needle 28a is relatively small and generally round and is connected to the arm 26a via a thread or very thin segment of mesh, e.g., by second needle connecting segment 26c. In FIG. 2b, e.g., the bullet needle 128a is bigger (than 28a) and round and is connected to the arm 126a via segment of mesh 126a. In FIG. 2c, e.g., the bullet needle 228a is bigger and flatter (than 28a and 128a) and is connected to the arm 226a via wider segment of mesh 226a. While the mesh 22 is preferably shaped as shown in FIG. 2, the mesh may be of any suitable shape and, generally, will incorporate a central body portion and at least two longitudinal side portions, e.g., arms. For example, the mesh of the present invention may be produced in a substantially oval shape or trapezium shape with extension arms and legs extending away from the central body portion of the mesh. The mesh is configured in this way so that it can be easily position over the pubocervical fascia and secured via the surrounding ligaments. Alternatively, the "needle" may be more densely formed mesh material. In such an embodiment, the small stainless steel needles may be replaced altogether. See, e.g., U.S. App. Pub. No. 2006/0052801.

The mesh material itself is preferably similar to the mesh material made by Boston Scientific Corporation called "POLYFORM™." Such a mesh is described in U.S. Patent Application Pub. No. 2005/0261545 incorporated herein by reference. There are many types of available mesh grafts such as the mesh described in PCT/US 02/31681 to Ethicon, also incorporated herein by reference. Nearly every medical device company has its own patented mesh and any of them can be used for this procedure.

The mesh preferably includes a plurality of open pores bounded by strands made of nonwoven polymeric material, for example, a polypropelene having monofilament fibers, wherein the junctions between the strands are without open interstices and the majority of open pores of the mesh have an area of less than 15 mm². Preferably, the pore size has an area of less than 10 mm². In the most preferred embodiments, the pore size of the central body portion of the mesh is greater than the pore size of the longitudinal side portions. The pore size range in these portions is preferably between 3 mm and 8 mm wide. The preferred mesh is also light and very flexible having a weight of less than 0.0080 g cm². The materials and mesh arrangement are such so as to minimize the chance of infection after implant.

While any conventional prosthetic material currently used for the treatment of pelvic organ prolapse can be employed when performing the inventive method, there are many so-called biografts that can be used as well such as animal or human donor tissue or any other xenograft material such as pig dermis, allograft, or homograft of skin, while any of these materials are suitable for reinforcing the vaginal wall, a synthetic polypropylene mesh is preferred.

While the inventive wing, leg, or arm of the graft is preferably affixed to a relatively small rounded bullet needle, it is also preferably tapered to allow atraumatic passage of it through the tissue and promote gripping of the wider portion of the arm or leg to the surrounding tissue. Further, instead of using the needle method for attaching the graft mesh, it is also possible for the mesh to be attached by other fastening means. Such a fastening means including a medical adhesive or glue, microwave or radio frequency welding, staples, tacks, and a hook and loop type fastener.

The second component is the graft delivery device or placement component as shown in FIGS. 3a-6. One of the novel concepts in this invention is the adaptation of a previously patented suture-passing device for the graft delivery device, e.g., U.S. Pat. Nos. 5,364,408; 5,540,704; 5,458,609; 5,575, 800, and 5,662,664. The modification of such a device allows the surgeon to use this device to pass the graft mesh's wings, e.g., the arms and legs, directly through the desired anchoring structures without have to traverse these pathways. Further, the inventive device itself is easier to use then the graft delivery devices currently in use in prolapse surgery. Therefore, the inventive device requires less skill to deliver the graft wings to their target location.

As mentioned, the inventive delivery device is preferably based in part on the "Capio™" device (see e.g., patent numbers above) which is sold by Boston Scientific. See also, e.g., U.S. Pat. Application Pub. No. 2006/0052801. The Capio™ device was originally patented as the Laurus™ device and is generally used elsewhere for suture passage in limited access cavities. The device is preferably a trocar capped by a curvi-linear needle guide and deployable bullet needle that passes to a catch mechanism. A plunger at the other end of the device deploys it.

Detailed drawings of an illustrative embodiment of the invention are shown in FIGS. 3a, 3b, 4a, 4b, 5a-d, and FIG. 6 wherein the graft delivery device 30 includes an outer housing 32, with finger grips 34a and 34b, and a deployment catch 36. The outer housing 32 is preferably made of injection molded plastic such as polycarbonate, as are many other of the components described herein. A deployment sleeve 38, slidably disposed within the outer housing 32, has a retention catch 40 and is attached to a pushrod 42, constructed for example, of stainless steel. A driver shaft 44 includes a button 46 and has a hole 48a, into which is bonded an elongate rigid shaft 50a. The rigid shaft 50a, which may be made of music wire, passes through outer housing ribs 52a, 52b, and 52c, terminates slidably disposed within a hollow cylinder 54a. The hollow cylinders 54a and 54b, preferably made from stainless hypodermic tubing, are held in recesses in the outer housing ribs 52b and 52c. An elongate flexible tubular member 56a, that may be made of polypropylene or other suitable material, is also slidably disposed within the hollow cylinder 54a. As shown in FIG. 6b, needle guide 58a may also be constructed from stainless hypodermic tubing, and has pivot pins 60a pivotally disposed within outer housing boss 62a. A driving link 64a is attached by a link pin 66 to the pushrod 42 and to the needle guide 58a by a pivot pin 68a, with the entire mechanism preferably made of stainless steel so as to maximize the biocompatibility as well as the strength of the actuating members.

Referring again to FIGS. 3a and 3b, the device 30 has a driver retainer 70 that is slidably disposed within the outer housing 32, and is fixably attached to rigid shafts 50a, with a hole 72 to allow the pushrod 42 to pass slidably therethrough. A driver spring 74, preferably wound from stainless steel wire is compressed between the driver retainer 70 and the outer housing rib 52b. A deployment spring 76, also made of stainless steel wire is compressed between an end 77 of the deployment sleeve 38 and outer housing rib 52a. A needle catch 78a is housed within a recess 80a in the outer housing 32.

Figure 4A:
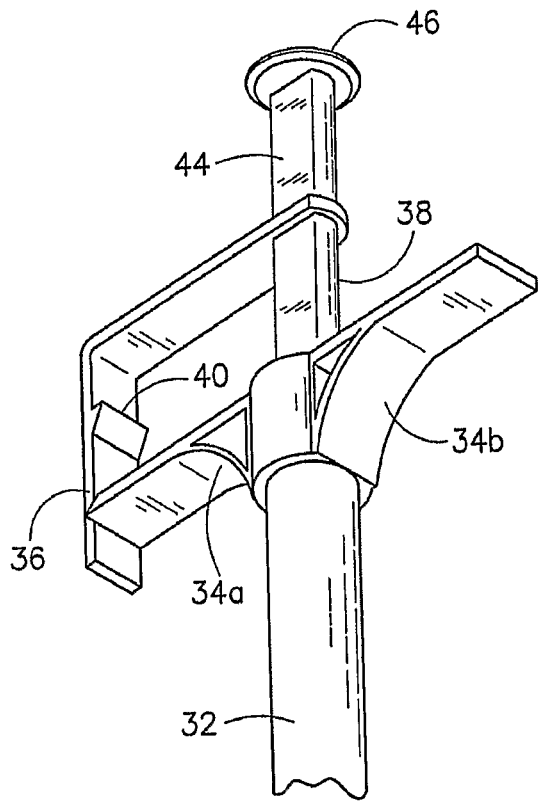
Figure 4B:
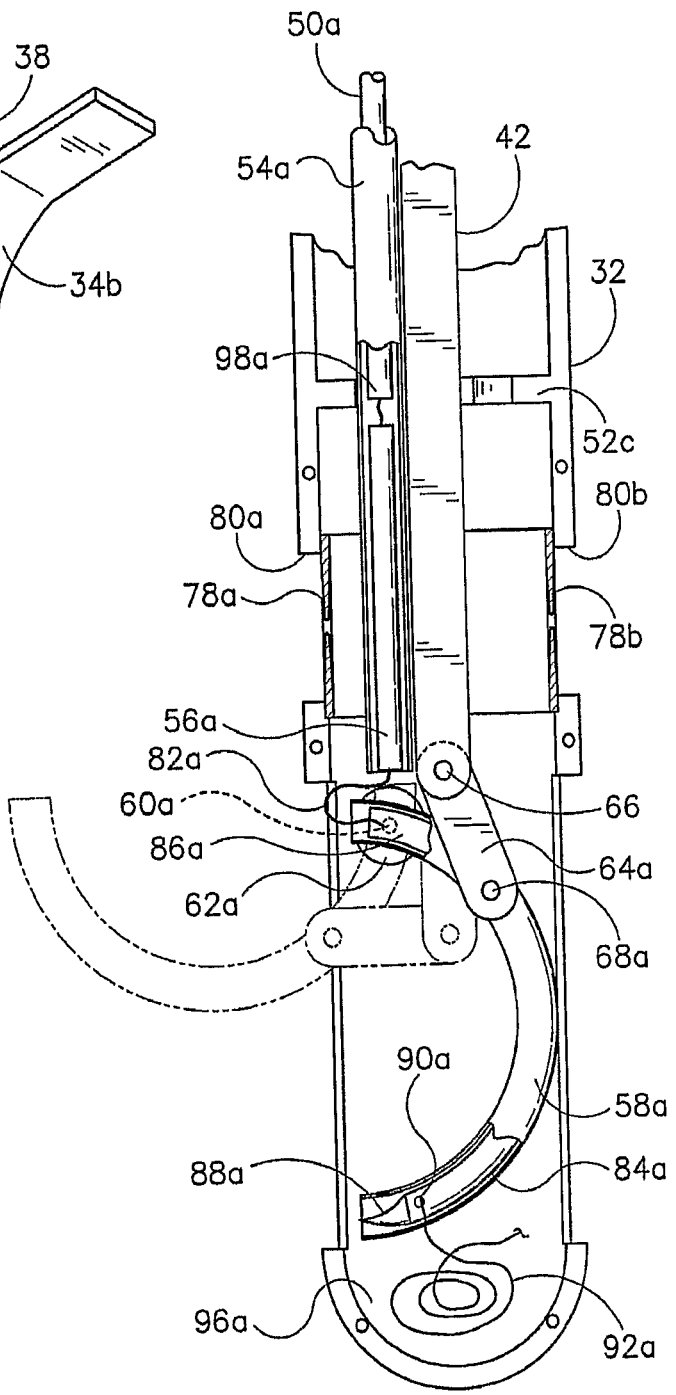

Referring now to FIG. 4b, a retraction line 82a that is preferably made of Kevlar™, is slidably threaded through the flexible tubular member 56a and is attached to a needle carrier 84a by means of a crimp 86a or other means that would bind the retraction line 82a to the needle carrier 84a. The distal end of the retraction line 82a is attached to the rigid shaft 50a by means of another crimp 98a or other means. The needle carrier 84a is slidably disposed within the needle guide 58a, and holds a needle 88a (or e.g. bullet needle 28a), typically constructed of surgical grade stainless steel in a recess 90a, such needle having a suture 92a attached thereto. The suture material is preferably polyglycolic acid, but may be made of polypropylene, nylon, silk, catgut, or any other materials known in the art selected for their biocompatibility and tensile strength to be used in the body for the approximation of tissue. The suture 92a exits the needle guide 58a by means of a groove 94a and is stored in a recess 96 in outer housing 32. In one preferred embodiment, suture 92a would be, e.g., thread 26c which is connected to arm 26a as shown in FIG. 2.

Figure 3A:
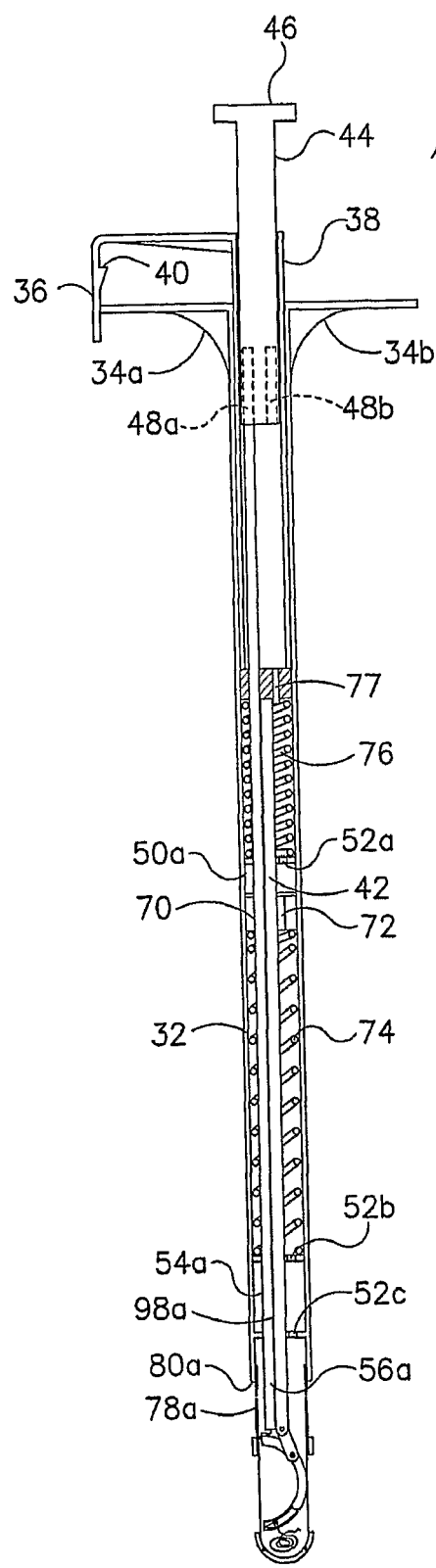
FIGS. 3a-3b show a graft placement component of the kit of the present invention.
Figure 3B:
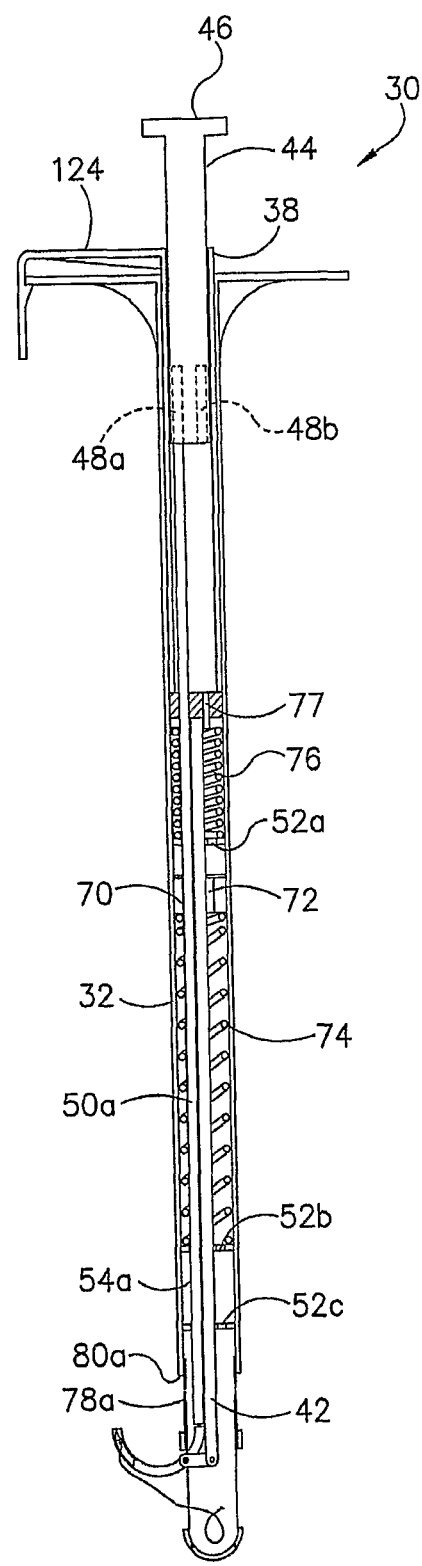

Referring to FIGS. 3b and 4b, arm 124 of deployment sleeve 38 is pushed so that the sleeve slides within the outer housing 32, compressing spring 76, and in turn sliding pushrod 42. When the pushrod 42 slides relative to the outer housing 32, driving link 64a, which is pivotally attached to both pushrod 42 and needle guide 58a, the pushrod 42 forces the needle guide 58a to pivot about the pin 60a that is retained in outer housing boss 62a.

One other embodiment of the present invention is shown in FIGS. 5a, 5b, 5c, 5d, and 6. It should be again understood that in the interest of clarity only one half of the instrument is being shown. The other half is quite similar in function and structure as the half described herein. The upper portion of the device is similar in construction and materials to the previously disclosed embodiments, and is not repeated here.

A mesh placement device 196 includes an outer housing 198 having bosses 200 into which a pin 202 is rotatably inserted. The pin 202 is secured to an arm 204, which is attached to a needle carrier 206. A pin 208 on needle carrier 206 is rotatably inserted into a hole 210 in a link 212. Another pin 214 is secured to a pushrod 216 and is rotatably inserted into another hole 218 in the link 212. The pushrod 216 is attached to a sleeve 220 slidably disposed within the outer housing 198.

FIG. 6 shows a detail view of a needle 222 (similar to bullet needle 28a) held in a recess 224 in the needle carrier 206. A thread 226, like thread 26c, is attached to the needle 222 and is threaded through a slot 228 in the needle carrier 206. All components in this mechanism are preferably constructed of surgical grade stainless steel, chosen for its biocompatibility and strength.

3. In Use

As mentioned above, there are specific anatomic structures, deep in the pelvis, typically used for graft fixation, which are chosen due to their advantageous location and resistance to displacement.

Nevertheless, because these structures are difficult to access, an incision must be made in the vaginal wall. See, e.g., FIGS. 7a and 7d. Once the incision is made, a delivery device 30 is used to put the graft, e.g., 22 in place. The delivery device 30 uses a needle, e.g., 28a that can be affixed to each one of the mesh arms or legs, e.g. 26a. The needle and graft are loaded into a needle guide located on the delivery device. Preferably, once the mesh and the needle are loaded in the delivery device, the remainder of the body of the mesh with the remaining three arms and legs hang from the needle. After the appropriate dissection of the paravaginal tissue is made and the anchoring structures are located and cleared of any connective tissue, the delivery device is moved into place over the desired structure. The plunger is then compressed and the needle deployed. Once the needle and mesh pass through the desired anchoring structure, the entire device 30 is gently retracted out of the vagina. This leaves the arm or leg of the mesh loosely encircling the anchoring point. The delivery device is then again held in position to engage the subsequent needles from each of the remaining three needles passing each wing around its anchoring point. The mesh can be delivered as a single piece or cut into two separate pieces for delivery into the anterior and posterior wall of the vagina separately. Adjustment of the arm or leg then can take place. This is done by pulling the mesh as cephalad as need be and causing the mesh to lie flat in its respective compartment. The ends of each arm or leg are then cut to release the needle. The excess mesh and needle are then disposed of. After closing the vagina, the pessary 123 is then inserted into the vagina and inflated to an appropriate degree. See, e.g., one possible embodiment shown in FIGS. 1a-1c. This accomplishes the goal of using the pessary to be retained in the vaginal wall and hold the mesh back into place. It does this while not being inflated to a degree that would impede blood flow or result in postoperative pain.

Turning now to FIGS. 7a-7d, posterior vaginal wall (213) is shown with the epithelium (214) of the posterior vaginal wall in place. In one preferred method of the present invention, a longitudinal incision is performed in order to mobilize the epithelium (214) off the underlying fascia (215). Dissection is carried out medially to the Levator Ani muscles on each side. In the upper part of the vagina, dissection is continued in a lateral and cranial direction through the peri-rectal space on both sides towards the Sacrospinous ligaments on each side. This creates a safe space through which to deploy the device. The pre-shaped mesh graft, e.g. 216, is designed for the posterior vaginal wall repair. It is placed over the recto-vaginal septum (215) with each extension arm (217, 218) placed into the space extending from the posterior vaginal wall dissection to the Sacrospinous ligament. The positioning of one possible embodiment of the mesh (216) is more clearly depicted in FIG. 8, which shows its location relative to the Sacrospinous ligament (233), the rectum (234) and the vagina (235).

The preferred intra-vaginal splint or pessary 123 is shown in FIGS. 1a-1c. The splint is preferably a rubber or silicone membrane. In one embodiment, the membrane is twin skinned and is inflatable. Inflation of the membrane with fluid e.g., air, is possible through tube 132a that provides a fluid channel into the space between the respective layers of the membrane. FIGS. 1a-1c shows a deflated intra-vaginal splint 123 preferably retained in the vagina before inflation. Like the embodiments shown in FIGS. 1a-1c, the embodiments of FIGS. 9a-9c can have a twin skinned configuration which enables its inflation. Optionally, one or more of base 130, shaft 135, and anchoring knob 137, depending on the intended end-use configuration, is hollow which enables inflation of respective portions or the entirety of pessary 123.

After inflation, the splint 123 can stay three (3) or more days and up to a period of four (4) weeks. Once this period has elapsed, the splint 123 can be removed by deflating it. After this time, the synthetic mesh should have become incorporated into the tissue of each of the respective vaginal walls.

While the preferred embodiments and best modes of utilizing the present invention have been disclosed above, other variations are also possible. For example, the materials, shape and size of the components may be changed.

Various alternatives are contemplated as being within the scope of the following claims that particularly point out and distinctly claim the subject matter regarded as the invention.

The invention claimed is:

1. A three dimensional pessary device for controlling a vaginal prolapse comprising:
    a base which defines a midsection thereof, the base having an arc configured to be approximately equal to a posterior axis deviation of a vagina and a horizontally ovoid cross-sectional shape;
    a first flange and a second flange which protrude from the midsection of the base;

an anchoring knob, distal the base, which is convex and configured to elevate a prolapsed wall of the vagina in a subject;

a pliable outer surface defining a hollow interior volume therein, and the pliable outer surface contiguous with the base, the first flange, the second flange, and the anchoring knob;

wherein the pessary device is configured to be at least partially disposed within the vagina, and wherein the pessary device is configured to assist in retaining a mesh implant proximate to the vagina.

2. The device of claim 1 wherein air is insertable into the hollow interior volume to inflate the pessary device.

3. The device of claim 1 wherein the prolapsed wall is an anterior wall of the vagina in the subject.

4. The device of claim 1 further comprising an inflation tube and an inflation device.

5. The device of claim 1 wherein the pliable outer surface includes dimples.

6. The device of claim 1 wherein the pliable outer surface includes bumps.

7. The device of claim 1 further comprising:

the pliable outer surface having a central depression extending into the pliable outer surface, and a surface texture selected from the group consisting of bumps and dimples; and an inflation tube receiving an inflation device at an end of the inflation tube; and wherein the prolapsed wall is an anterior wall of the vagina in the subject.

8. A three dimensional pressary device for controlling a vaginal prolapse comprising:

a base which defines a midsection thereof, the base having an arc configured to be approximately equal to a posterior axis deviation of a vagina;

a first flange and a second flange which protrude from the midsection of the base;

an anchoring knob, distal the base, configured to engage a prolapsed wall of the vagina in a subject; and wherein at least one of the first and second flanges is inflatable.

9. The device of claim 8 further comprising a central depression which extends into a pliable outer surface of the pressary device, the pliable outer surface defining a hollow interior volume therein.

10. The device of claim 8 wherein the anchoring knob is convex and elevates an anterior vaginal wall in the subject.

11. The device of claim 8 further comprising an inflating tube and an inflation device.

12. The device of claim 8 further comprising a pliable outer surface including dimples.

13. The device of claim 8 further comprising a pliable outer surface including bumps.

14. The device of claim 8 further comprising:

a pliable outer surface having a central depression extending into the pliable outer surface, and a surface texture selected from the group consisting of bumps and dimples; and an inflation tube receiving an inflation device at an end of the inflation tube; and wherein the anchoring knob is convex and elevates an anterior vaginal wall in the subject.

15. The device of claim 8 wherein the base has a horizontally ovoid cross-sectional shape.

* * * * *